United States Patent
Barnes et al.

(10) Patent No.: US 6,923,982 B2
(45) Date of Patent: Aug. 2, 2005

(54) CALENDERED HYDROCOLLOID DRESSING

(75) Inventors: Scott C. Barnes, Renfrew (CA); Jim Jian Ling Ding, Glastonbury, CT (US)

(73) Assignee: Scapa North America, Windsor, CT (US)

( * ) Notice: Subject to any disclaimer, the term of this patent is extended or adjusted under 35 U.S.C. 154(b) by 0 days.

(21) Appl. No.: 09/925,063

(22) Filed: Aug. 8, 2001

(65) Prior Publication Data

US 2002/0106400 A1 Aug. 8, 2002

Related U.S. Application Data

(60) Provisional application No. 60/225,717, filed on Aug. 16, 2000.

(51) Int. Cl.[7] ................................................. A61F 13/00
(52) U.S. Cl. ..................... 424/442; 424/444; 424/445; 424/446; 424/447; 424/448; 424/449
(58) Field of Search ................................ 424/443–449, 424/400, 800

(56) References Cited

U.S. PATENT DOCUMENTS

| 4,186,165 A | 1/1980 | Aberson et al. |
| 4,793,337 A | 12/1988 | Freeman et al. |
| 4,994,278 A | * 2/1991 | Sablotsky et al. .......... 424/447 |
| 5,059,189 A | * 10/1991 | Cilento et al. ................ 156/66 |
| 5,372,819 A | * 12/1994 | Godbey et al. ............. 424/443 |
| 5,833,642 A | 11/1998 | McCabe et al. |

FOREIGN PATENT DOCUMENTS

| EP | 0512 855 A2 | 11/1992 |
| WO | WO 98/09664 | 3/1998 |

OTHER PUBLICATIONS

PCT International Search Report from PCT/US 01/24961, Applicant: Scapa Tapes N.A.

* cited by examiner

Primary Examiner—Thurman K. Page
Assistant Examiner—Isis Ghali
(74) Attorney, Agent, or Firm—Claude L. Nassif; Peter Jon Gluck; Greenberg Traurig LLP

(57) ABSTRACT

A calendered hydrocolloid dressing for the wound care and a one step method of manufacturing the hydrocolloidal dressing are described. In particular, the invention is concerned with a hydrocolloid dressing which is absorbent, non-damaging to the skin and comfortable to the user preferably having at least a thermoplastic elastomer backing and water absorbent polymeric adhesive layer.

35 Claims, 1 Drawing Sheet

CALENDERED HYDROCOLLOID DRESSING

This application claims the benefit of Provisional Application No. 60/225,717, filed Aug. 16, 2000.

BACKGROUND OF THE INVENTION

Field of the Invention

This invention relates to a calendered hydrocolloid dressing for the wound care and a method of manufacturing the hydrocolloidal dressing. In particular, the invention is concerned with a hydrocolloid dressing which is absorbent, non-damaging to the skin and comfortable to the user. Further, the invention is concerned with economical and efficient manufacturing of the hydrocolloid dressing.

Wound care is desirable to improve the health and appearance of underlying dermal tissues. Wounds, either injury induced, such as cuts, abrasions or blisters, or surgically induced, such as surgical incisions or ostomies, for example require localized treatment to remedy the affected area and to prevent further dermal damage. If wounds are not properly treated, further dermal irritation can occur resulting in secondary infections and further discomfort to the patient.

Hydrocolloid dressings are widely used in the area of wound and ostomy care due their beneficial effects to the healing process. Particularly, hydrocolloid dressings are beneficial to wound healing in that hydrocolloids absorb excess fluids away from the wound site, maintain a moist environment for the wound, offer a controlled adhesion level to the wound bed, which allows a non-invasive dressing change without causing trauma to the wound, and thus facilitate the healing process.

Recently, the use of hydrocolloid dressings has spread beyond just the hospital setting and are now commonly found at the retail level for general consumer use. Products designed for over the counter use are often somewhat thinner in hydrocolloid mass and are not designed to provide a particularly high level of fluid absorption capability. However, hydrocolloid dressings used for wound care and ostomy applications require a high degree of absorbency along with good structural integrity of the hydrocolloid mass, but are often bulky and uncomfortable to the user. In either case, the hydrocolloid dressing should not further aggravate the primary wound by causing further dermal irritation.

Therefore, there is a need for a hydrocolloid dressing which provides enhanced absorbency and/or enhanced structural integrity and/or enhanced patient comfort. Further, there is a need for a method of manufacturing the hydrocolloid dressing efficiently and economically to achieve at least the described properties.

SUMMARY OF THE INVENTION

The invention provides a calendered hydrocolloid dressing which has improved advantages over known dressings for wound care. There is also provided a method for manufacturing calendered hydrocolloid dressings. A calendered hydrocolloid dressing manufactured in the method described has improved film strength, particularly when the dressing is saturated. Further, the hydrocolloid dressing manufactured in the method described has improved dimensional stability. Finally, the process of manufacturing calendered hydrocolloid dressings is more efficient and economical relative to other prior art methods, at least because there are fewer stages of mixing and fewer components of manufacture required.

According to the invention, there is provided a hydrocolloid dressing for wound care having a surface area for adhering to the epidermis, dermis or wound area (skin) and comprises a backing film layer, having an upper and lower surface area, and an adhesive adhered on the lower surface area of the backing film layer. In some embodiments, the backing film layer is comprised of material including copolymers, and more particularly ethylene methyl acrylate. In some embodiments, the backing film layer is comprised of up to 100% ethylene methyl acrylate copolymer, of which about 21% is comonomer. The backing film layer is a substrate which is preferably flexible.

The adhesive is any substance which holds the patch in contact with the dermis or wound site. Preferably the adhesive is a polymeric adhesive composition, and more preferably a pressure sensitive adhesive. Preferably components of the adhesive are water absorbent.

In some embodiments, the adhesive contains therapeutic agents which aid in treating or healing the wound and therapeutic agents can be a single agent or a combination of agents. Further, the adhesive is selected to have a desired property of not interfering with the action of water absorbent components and/or the delivery of the therapeutic agent to the wound.

The hydrocolloid dressing can be made in a variety of shapes, and the dressing in its entirety or any component thereof can have any combination of height, width and depth. At least one of and preferably both of the backing film layer and adhesive layer can be substantially transparent or clear so as to permit inspection of the wound without removing the dressing, or a flesh-like color or shade so as to effectively blend with the skin of user.

Preferably, the hydrocolloid dressing is manufactured using a calender process to form the backing film and apply the adhesive layer to the backing film lower surface. Further, the calender process used to manufacture the hydrocolloid can be carried out in the absence of a release liner. However, after the manufacture of the hydrocolloid dressing, a release liner can be applied to the adhesive layer lower surface area to facilitate conversion of the dressing, or to protect the adhesive before application of the dressing to the user, for example.

The foregoing and other objects, features, and advantages of the present invention will be apparent from the following detailed description of the preferred embodiments which makes reference to several drawing figures.

DETAILED DESCRIPTION OF THE PREFERRED EMBODIMENTS

In the following description of the preferred embodiments reference is made to the accompanying drawings which form the part thereof, and in which are shown by way of illustration of specific embodiments in which the invention can be practiced. It is to be understood that other embodiments can be utilized and structural and functional changes can be made without departing from the scope of the present invention.

Figure 1:
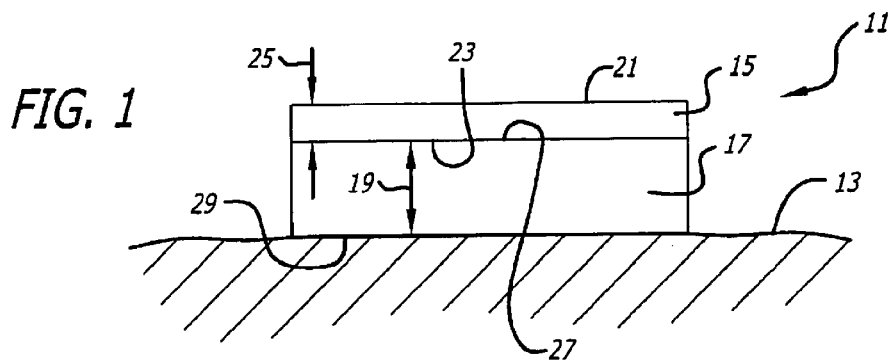
FIG. 1 is a perspective view of the hydrocolloid dressing being applied to the skin.

The calendered hydrocolloid dressing 11 is for the treatment and/or protection of a wound when applied to the skin 13 of the user (FIG. 1). As illustrated in FIG. 1, in one embodiment, the hydrocolloid dressing 11 includes at least a backing film layer 15 having an adhesive layer 17 adhered to the underside. When applied to the user, the hydrocolloid dressing lower surface area 19 is in contact with the user's skin 13.

Calendered Hydrocolloid Dressing

Backing Film Layer

The hydrocolloid dressing 11 includes a backing film layer 15 having an upper surface area 21 and a lower surface area 23, and constitutes a thickness 25; and an adhesive layer 17 adhered to the backing film layer lower surface area 23. The adhesive layer 17 has an upper surface area 27 and a lower surface area 29, and constitutes a thickness 19. In use, the adhesive lower surface area 29 is adhered to the skin 13 of the user.

The backing film layer materials which are useful for this invention are not particularly limited as long as they can provide a suitable substrate for the adhesive layer 17 and are sufficiently strong to withstand removal from the skin 13 and maintain its integrity, having been secured to the skin 3 by the adhesive layer 17. Preferably, the backing film layer is water impervious.

The backing film layer 15 is preferably flexible from the viewpoint of comfort. The flexibility is achievable by elasticity in any one or all axes of the material. Further, the backing film layer 15 is preferably pliable to accommodate skin contours, when applied to areas of skin having alterations in surface angles. The backing is preferably non-stretchable, namely non-elastic, in the planar axis of the material.

The backing film layer of the hydrocolloid dressing 11 preferably includes a thermoplastic elastomer, and more specifically an ethylene based copolymer. Examples of ethylene based copolymers which may be used in this invention include, but are not limited to, ethylene acrylic acrylate, ethylene butyl acrylate, ethylene ethyl acrylate and ethylene methyl acrylate copolymer (EMAC). In one embodiment, the backing film is preferably about 50% to about 100% ethylene based copolymer. The ethylene based copolymers used in the backing preferably have comonomer levels of about 8–28% and most preferably about 21%. The levels of comonomer in the ethylene based copolymer of the backing film layer 15 can be selected to achieve a pliable backing which is comfortable for the user to wear. Further, the ethylene based copolymers used are preferably in the range of about 2 to about 10 melt index (MI) resins, however as is appreciated by those skilled in the art other grades of ethylene based copolymer could be used. Examples of ethylene based copolymer which can be used for the backing include, but are not limited to EMACs, such as Chevron SP2205, Exxon Optema® TC-110 and Exxon Optema® TC-120.

Further, the backing film layer 15 can include a low density polyethylene homopolymer (LDPE). The addition of LDPE may be advantageous at least in improving the processing speed by increasing the melt strength of the calendered film. A wide range of LDPEs can be used in the backing. The LDPEs used in the backing are preferably in the rage of about 2 to about 16 MI extrusion and/or coating grade resins. Examples of LDPEs which can be used in the backing film layer 15 include, but are not limited to Nova Chemicals LF-0219-AM or Chevron PE1019.

The backing film layer 15 can further include additives, such as antioxidant/stabilizer and/or processing aids. Hindered phenolic antioxidant such as Irganox® 1010 manufactured by Ciba-Geigy is an example of an appropriate stabilizer for medical applications. Processing aids such as N,N' Ethylene Bisstearamide may be advantageous at least in benefiting the processing by assisting in the release of the calendered film from the center roll surface. Use of processing aids is particularly preferable in backing film formulations where the comonomer level exceeds 18%. An example of one such additive is Acrawax® C manufactured by Lonza Specialty Chemicals. In an alternate embodiment the backing film is a composition of about 65% to about 100% by weight EMAC, up to about 35% by weight LDPE, about 0.05 to about 2% by weight antioxidants, processing aids and/or stabilizers.

The backing film layer 15 is also preferably of a thickness 25 to provide sufficient strength to the dressing 11, but also of a thinness which will be comfortable to the wearer and pliable to contact all skin surfaces 3. In one embodiment, the backing film layer thickness 25 is about 0.5 to about 10 thousands of and inch (mils), and in other embodiments, the thickness of the backing film layer is about 2 to about 6 mils. The backing film layer thickness 25 can or can not be constant from the backing film upper surface area 21 to the backing film lower surface area 23.

Adhesive Layer

An adhesive useful in this invention is any substance which holds the hydrocolloid dressing 11 in contact with the skin 13, and also absorbs fluid away from the surface of the skin 13 and into the adhesive layer 17 of the hydrocolloid dressing 11. The adhesive layer 17 can be located on any part of, or the entirety of, the backing film layer lower surface area 23.

A wide range of adhesive materials can be used for the hydrocolloid dressing, and can be selected to maximize adhesion, absorption and comfort, while minimizing irritation to the user. The adhesive layer 17 is preferably efficient at adhering to, but not damaging to the dermis or wound site 13. The adhesive layer 15 further preferably has a relatively greater adherence to the backing film layer 15 than to the dermis or wound site 13. There can be a desired range of adhesive strength for the adhesive layer 15 in the present invention. The strength can vary relative to the selected use of the hydrocolloid dressing 11.

The adhesive layer 15 is preferably comprised of a polymeric adhesive composition. In one preferred embodiment, the polymeric adhesive composition comprises a pressure sensitive polymer mixture. In some embodiments, rubber based polymer adhesives can be used. Examples of polymer adhesives which may be used include, but are not limited to block copolymers (such as styrene-isoprene-styrene copolymers and styrene-ethylene/butylene-styrene copolymers), butyl and polyisobutylene (PIBs).

Examples of butyl rubber, include, but are not limited to Butyl 268 & 269 (Exxon Mobile Chemical Co., Houston, Tex., USA) may be used at least to improve the integrity of hydrocolloid dressing. Examples of PIBs suitable for use in the invention include, but are not limited to PIB 6H (Nippon Petrochemicals Co., Ltd., Tokyo, Japan) and Vistanex (Exxon Mobile Chemical Co., Houston, Tex., USA). In some embodiments, PIB grades can have average molecular weight in a range of 36000 to 70000. By way of example, Vistanex LM-MH (Flory Molecular Weight 50,400–55,800) may be particularly useful in this invention.

Hydrocolloid. Regardless of the adhesive system used, the adhesive layer 17 also includes a hydrocolloid. Hydrophilic particles can be added to the adhesive composition and are preferably capable of swelling in water and transporting water. Hydrophilic particles which may be used in the invention include, but are not limited to naturally derived substances (such as silica, collagen, pectin, gelatin, starches, guar gum, gum arabic, locust bean gum, gum karaya, alginic acid and its sodium or calcium salts) and synthetic substances (such as such as sodium carboxymethylcellulose (CMC), crosslinked sodium carboxymethylcellulose, crystalline sodium carboxymethyl cellulose, polyvinyl alcohol, polyvinyl pyrollidone, high molecular weight polyethylene glycols and polypropylene glycols, cross-linked dextran and starch-acrylonitrile graft copolymer, starch sodium polyacrylate, gluten, polymer of methyl vinyl ether and maleic acid and derivatives; polyvinyl pyrrolidone, polyethylene glycols, polypropylene glycols, metal and/or ammonium salts of polyacrylic acid and/or its copolymers, and metal or ammonium salts of polystyrene sulfonic acid) or a variety of alternative commercially available absorbent products.

Additives. Further, the adhesive layer 17 can also contain additives, such as tackifiers, plasticizers and/or stabilizers to achieve the desired adhesive properties. Examples of plasticizers include, Parapol (Exxon Mobile Chemical Co., Houston, Tex., USA), a polybutene, and Eastoflex E1003 or 1060, resins (Eastman Chemical, Kingsport, Tenn., USA).

In some embodiments, the adhesive layer 17 can include therapeutic agents as additives, including those which can assist with wound protection and healing, such as alcohol, peroxide or betadine; antimicrobials; antibacterials, such as Triclosan, or polysporin; antivirals, such as Nonoxyl-9; antifungals, such as imidazole; antinflamatories such as hydrocortizone; wound healing promoters, such as growth factors; collagen; moisturizers, such as aloe or vitamins A, D or E; anti-scaring medications such as cortisone or pharmacologically active agents, including, but not limited to, analgesics, anesthetics, anti-inflammatories, and steroids. During processing of the adhesive layer active agents may be combined with either the polymeric composition, with the hydrocolloid, or both, for example. In another example, the active agent may be adhered to at least a portion of the adhesive lower surface are 29.

In one embodiment, the adhesive layer 17 is comprised of about 15% to about 40% polymer, about 10% to about 50% hydrocolloid particles, about 10 to about 75% of additives. In another embodiment, the adhesive material is a composition of about 20–30% polymer, about 25–35% hydrocolloid particles, about 40–50% of additives. A typical hydrocolloid composition comprises of 100 parts of Vistanex LM-MH, 20 parts of Butyl 268, 12 parts of Parapol 1300, and 40 parts of sodium CMC.

The adhesive layer thickness 19 is preferably thick enough to afford suitable adhesion to and absorption from the dermis or wound site 13. In one embodiment, the adhesive layer thickness 19 is about 5 to about 50 mils, and in other embodiments, the thickness of the adhesive is about 10 to about 30 mils. The adhesive layer thickness 19 can or can not be constant from the adhesive layer upper surface area 27 to the adhesive layer lower surface area 29.

Release Liner

Due to the novel calendering process used to manufacture the hydrocolloid dressing 11, manufacturing can be carried out in the absence of a release liner. However, after the manufacture of the hydrocolloid dressing 11 a release liner 31 can be laminated to the adhesive layer lower surface area 29 to facilitate conversion of the dressing (such as by die cutting) or to protect the adhesive before application to the user, for example. Examples of suitable liner materials include, but are not limited to bleached Kraft-Glassine paper, silicone coated on one side at least where contact with the adhesive layer is made.

Figure 2:
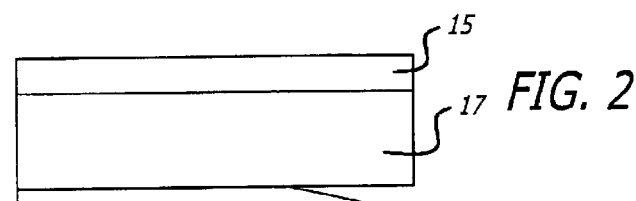
FIG. 2 is a perspective view of one embodiment of the hydrocolloid dressing having a release liner.

The liner 31 can be of the same dimensions as the hydrocolloid dressing 11, or can be of different dimensions to facilitate removal of the liner 31 from the dressing 11. Where the liner 31 is of different dimensions as the dressing, the liner can be larger in any one or all planar dimensions than the dressing (FIG. 2). Further, the liner 31 can have lines of weakness, such as scores or perforations, so as to facilitate removal of the liner from the dressing.

Method of Manufacture of the Hydrocolloid Dressing

The method of manufacturing for the dressing can be achieved, but is not limited to the method or order of operations as described below.

Figure 3:
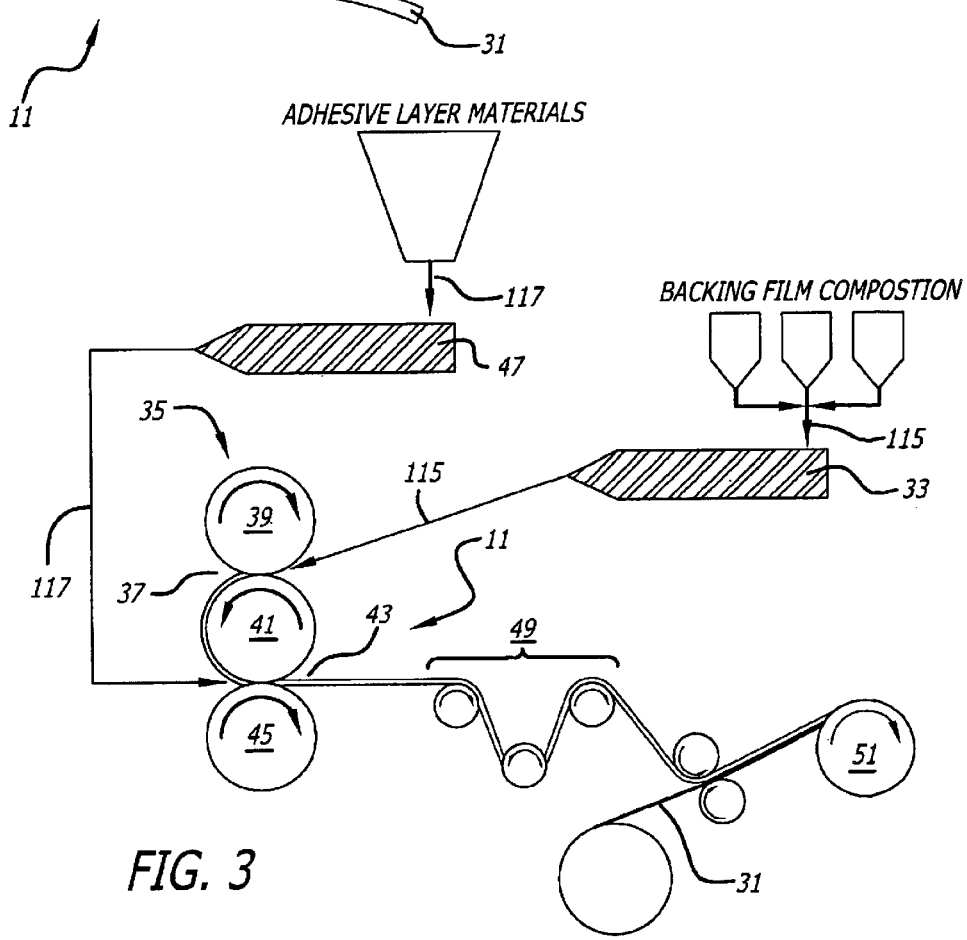
FIG. 3 is a diagrammatic view of one method for manufacturing the hydrocolloid patch.

In one method of manufacturing the hydrocolloid dressing 11, a multi-roll calender process is used to form the backing film layer 15 and apply the adhesive layer 17 in a single manufacturing step (FIG. 3). The backing film composition 115 is formed by blending the selected polymers, antioxidants, processing aids and/or stabilizers in selected proportions that are metered, mixed and extruded, via a single screw extruder 33, for example. The temperature of the backing film composition 115 when extruded is preferably in the range of about 350–400° F., and most preferably about 380° F. The backing film composition 115 is delivered to the multi-rolled calender 35 in a continuous fashion for forming into the backing film layer 15. The backing film layer thickness 25 is determined by the width of the top gap 37 between the calender top roll 39 and center roll 41.

The calender top roll 39 surface temperature is preferably heated to the temperature of the backing film composition 115, while the center roll 41 is cooled relative to the temperature of the extrudate. Further, the top roll 39 preferably rotates at a slower rate relative to the center roll 41. The backing film composition 115 preferably sticks to the cooler and faster center roll 41 and is carried to the lower gap 43 between the calender center roll 41 and the lower roll 45 to be laminated with adhesive layer 17. The total thickness (at least the adhesive layer thickness 19+the backing layer thickness 25) of the hydrocolloid dressing 11 is determined by the width of the lower gap 43 between the calender center roll 41 and lower roll 45.

Next, the adhesive composition 117 is prepared for extrusion on to the calender. As is appreciated by those skilled in the art, adhesives can be prepared in a number of ways and in a variety of mixing devices. For example, batch mixers (such as internal, sigma blade mixers including an AMK Mixtruder®) can be used to mix the rubber-based adhesives prior to the calendering step. Secondary operations can be used to prepare the adhesive off-line when batch mixing is used. Alternatively, continuous mixers (such as a Farrel Continuous Mixer (FCM)®) or twin screw extruders can be used. Continuous mixing typically allows for the adhesive can be mixed and fed to the calender directly. Preferably, the final delivery of the adhesive composition 117 to the calender 35 is accomplished by extrusion, with a single screw extruder 47 or melt pump system for example. The temperature of the adhesive composition 117 when extruded is preferably in the range of about 260–320° F., and most preferably about 290° F.

The method of manufacturing for the adhesive composition can be achieved, but is not limited to the method or order of operations as described below. For example, adhesive composition ingredients including PIB and Butyl rubber, may be added in a sigma blade mixer and heated to about 150° C. under nitrogen blanket. The ingredients are preferably heated until they are completely melted, and additionally the Parapol then added. The mixture is preferably mixed until the composition is homogeneous. The temperature is preferably reduced to about 120° C. Hydrophilic particles may then be blended into the heated adhesive composition and mixing continued until the particles are mixed uniformly throughout. The mixture is then discharged from the mixer and ready for calendering.

The adhesive composition 117 is calendered onto the backing film layer 15 between the center roll 41 and lower roll 45. A wide range of adhesive thickness 19 can be achieved by this method. The lower roll 45 is preferably heated to the temperature of the adhesive composition 117 when extruded. Further, the lower roll 45 preferably rotates at a slower rate relative to the center roll 41.

Once laminated, the hydrocolloid dressing 11 is stripped from the calender and preferably conveyed through a cooling section 49.

The adhesive lower surface 29 may then laminated with a release liner 31, and wound on to a master roll 51 for converting the hydrocolloid dressing material into individual use patches by cutting or pressing the dressings into the desired shapes and packing them for distribution to the user. A release liner 31 may, but need not be added, at any time after the product has been manufactured, for conversion or for distribution to the user (see FIG. 3).

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. Further, with respect to the claims, it should be understood that any of the claims described below can be combined for the purposes of the invention.

EXAMPLE 1

| Backing film composition: | % (weight) | Adhesive composition: | % (weight) |
|---|---|---|---|
| EMAC - Exxon Optema TC-110 | 99.8 | Vistanex LM-MH | 58 |
| Antioxidant | 0.1 | Butyl 268 | 12 |
| Acrawax C | 0.1 | Parapol 1300 | 7 |
|  |  | Sodium CMC | 23 |

A 15 mil calendered hydrocolloid dressing was produced that consisted of a 5 mil backing film layer and a 10 mil adhesive layer. The hydrocolloid dressing was laminated with a silicone coated release liner at the point of windup. The coated product was subsequently die cut for the purpose of field testing.

EXAMPLE 2

| Backing film Composition: | % (weight) | Adhesive composition: | by parts |
|---|---|---|---|
| EMAC - Exxon Optema TC-110 | 85.0 | Vistanex LM-MH | 58 |
| LDPE - Novacor LF-0219-AM | 14.9 | Butyl 268 | 12 |

-continued

| Backing film Composition: | % (weight) | Adhesive composition: | by parts |
|---|---|---|---|
| Antioxidant | 0.1 | Parapol 1300 | 7 |
|  |  | Sodium CMC | 23 |

A 35 mil calendered hydrocolloid dressing was produced that consisted of a 5 mil backing film layer and a 30 mil adhesive layer. The product was laminated with a silicone coated release liner at the point of windup. The coated product was subsequently die cut for the purpose of field testing.

While the specification describes particular embodiments of the present invention, those of ordinary skill can devise variations of the present invention without departing from the inventive concept.

What is claimed is:

1. A method of manufacturing a calendered hydrocolloid dressing comprising the steps of:
    a. blending a backing film composition, said backing film composition including an ethylene based copolymer;
    b. extruding the backing film composition;
    c. calendaring the backing film composition between a top roll and a center roll to form a backing film layer;
    d. blending a polymeric pressure-sensitive adhesive composition, said polymeric pressure-sensitive adhesive composition including a hydrocolloid; and
    e. calendaring the adhesive composition between the center roll and a lower roll to from a hydrocolloid dressing comprising a backing film layer and an adhesive layer wherein the polymeric pressure-sensitive adhesive composition is applied and calendered directly onto the backing film layer such that formation of an adhesive layer of said polymeric pressure-sensitive adhesive composition and lamination of said adhesive layer to said backing film layer is achieved in a single manufacturing step.

2. The method of claim 1, further comprising the step of adhering a release liner layer to a lower surface area of the hydrocolloid dressing.

3. The method of claim 1, wherein said ethylene based copolymer is one or a combination of any of an ethylene acrylic acrylate, ethylene butyl acrylate, ethylene ethyl acrylate or ethylene methyl acrylate copolymer.

4. The method of claim 1, wherein the backing film layer is comprised of about 100% by weight ethylene-based copolymer, wherein the ethylene-based copolymer is about 21% by weight comonomer.

5. The method of claim 1, wherein material comprising the backing film layer further includes low density polyethylene homopolymer.

6. The method of claim 1, wherein material comprising the backing film layer further includes additives.

7. The method of claim 6, wherein the additives are selected from the group consisting of antioxidants, stabilizers and processing aids.

8. The method of claim 1, wherein the backing film layer is comprised of about 65% to about 100% by weight ethylene methyl acrylate copolymer, from about 0 to about 35% by weight low density polyethylene, about 0.05 to about 2% by weight of any one of or combinations of any of antioxidants, processing aids or stabilizers.

9. The method of claim 1, wherein the polymeric pressure sensitive adhesive composition comprises at least one rubber.

10. The method of claim 9, wherein the rubber is any one of or a combination of any one of styrene-isoprene-styrene copolymers, styrene-ethylene-styrene copolymers, styrene-butylene-styrene copolymers, butyl rubber and polyisobutylene.

11. The method of claim 1, wherein the adhesive layer further comprises at least one additive.

12. The method of claim 11, wherein the additive is any one or a combination of any of tackifiers, stabilizers, plastifiers, processing aids or therapeutic agents.

13. The method of claim 1, wherein the adhesive layer comprises about 15% to about 40% by weight polymer, about 10% to about 50% by weight hydrocolloid, and about 10 to about 75% of by weight additives.

14. The method of claim 1, wherein the adhesive layer comprises about 58% by weight polyisobutylene, about 12% by weight butyl rubber, about 7% by weight plasticizer and 23% by weight hydrocolloid.

15. The method of claim 1, wherein the adhesive layer, backing film layer, or adhesive and backing film layer are substantially transparent or clear.

16. The method of claim 1, wherein the adhesive layer, backing film layer, or adhesive and backing film layer are substantially flesh colored.

17. The method of claim 1, wherein the adhesive layer is about 5 to about 50 mils and wherein the backing film layer is about 0.5 to about 10 mils.

18. A method of manufacturing a calendered hydrocolloid dressing comprising the steps of:
   a. blending a backing film composition containing an ethylene-based copolymer;
   b. extruding the backing film composition;
   c. calendering the backing film composition between a first roll and a second roll to form a backing film layer;
   d. blending a polymeric pressure-sensitive adhesive composition containing hydrocolloids; and
   e. calendering the polymeric pressure-sensitive adhesive composition between the second roll and a third roll to form a hydrocolloid dressing comprising a backing film layer and an adhesive layer, wherein the polymeric pressure-sensitive adhesive composition is introduced and calendered directly onto the backing film layer such that formation of an adhesive layer of said polymeric pressure-sensitive adhesive composition and lamination of said adhesive layer to said backing film composition is achieved in a single manufacturing step.

19. A method of manufacturing a calendered hydrocolloid dressing comprising the steps of:
   a. blending a thermoplastic elastomeric backing film composition;
   b. extruding the thermoplastic elastomeric backing film composition;
   c. calendering the thermoplastic elastomeric backing film composition between a first roll and a second roll to form a backing film layer;
   d. blending an a polymeric pressure-sensitive adhesive composition containing hydrocolloids; and
   e. extruding and then calendering the polymeric pressure-sensitive adhesive composition between the second roll and a third roll to form a hydrocolloid dressing comprising a backing film layer and an adhesive layer, wherein the polymeric pressure-sensitive adhesive composition is applied and calendered directly onto the backing film layer such that formation of an adhesive layer of said polymeric pressure-sensitive adhesive composition and lamination of said adhesive layer to said backing film layer is achieved in a single manufacturing step.

20. The method of claim 19, further comprising the step of adhering a release liner layer to a lower surface area of the hydrocolloid dressing.

21. The method of claim 19, wherein said thermoplastic elastomeric backing film composition is an ethylene based copolymer.

22. The method of claim 21, wherein said ethylene based copolymer is one or a combination of any of an ethylene acrylic acrylate, ethylene butyl acrylate, ethylene ethyl acrylate or ethylene methyl acrylate copolymer.

23. The method of claim 19, wherein the backing film layer is comprised of about 100% by weight copolymer, wherein the copolymer is about 21% by weight comonomer.

24. The method of claim 19, wherein the backing film layer further includes low density polyethylene homopolymer.

25. The method of claim 19, wherein the backing film layer further includes additives.

26. The method of claim 25, wherein the additives are selected from the group of antioxidants, stabilizers and processing aids.

27. The method of claim 19, wherein the backing film layer is comprised of about 65% to about 100% by weight ethylene methyl acrylate copolymer, from about 0 to about 35% by weight low density polyethylene, about 0.05 to about 2% by weight of any one of or combinations of any of antioxidants, processing aids or stabilizers.

28. The method of claim 19, wherein the polymeric pressure sensitive adhesive composition comprises at least one rubber.

29. The method of claim 28, wherein the rubber is any one of or a combination of any one of styrene-isoprene-styrene copolymers, styrene-ethylene-styrene copolymers, styrene-butylene-styrene copolymers, butyl rubber and polyisobutylene.

30. The method of claim 19, wherein the adhesive layer further comprises at least one additive, wherein the additive is any one or a combination of tackifiers, stabilizers, plastifiers, processing aids or therapeutic agents.

31. The method of claim 19, wherein the adhesive layer comprises about 15% to about 40% by weight polymer, about 10% to about 50% by weight hydrocolloid, and about 10 to about 75% of by weight additives.

32. The method of claim 19, wherein the adhesive layer comprises about 58% by weight polyisobutylene, about 12% by weigh; butyl rubber, about 7% by weight plasticizer and 23% by weight hydrocolloid.

33. The method of claim 19, wherein the adhesive layer, backing film layer, or adhesive and backing film layer are substantially transparent or clear.

34. The method of claim 19, wherein the adhesive layer, backing film layer, or adhesive and backing film layer are substantially flesh colored.

35. The method of claim 19, wherein the adhesive layer is about 5 to about 50 mils and wherein the backing film layer is about 0.5 to about 10 mils.

* * * * *

UNITED STATES PATENT AND TRADEMARK OFFICE
CERTIFICATE OF CORRECTION

PATENT NO. : 6,923,982 B2
DATED : August 2, 2005
INVENTOR(S) : Barnes et al.

It is certified that error appears in the above-identified patent and that said Letters Patent is hereby corrected as shown below:

Column 5,
Line 30, the word "antinflamatories" should be corrected to read as
-- anti-inflammatories --.

Column 6,
Line 24, the period should be removed from the phrase "350-400° F.," to read
-- 350-400° F, --.
Line 59, the period should be removed from the phrase "260-320° F.," to read
-- 260-320° F, --.
Line 66, the period should be removed following "150° C".

Column 7,
Line 18, the word -- be -- should be added after the word "then", so as to read "may then be laminated with...".

Column 8,
Lines 25 and 30, the word "calendaring" should be -- calendering --.

Column 10,
Line 52, the word "weigh" should be -- weight --.

Signed and Sealed this

Twenty-fifth Day of October, 2005

JON W. DUDAS
*Director of the United States Patent and Trademark Office*